US005084268A

United States Patent [19]
Thaler

[11] Patent Number: 5,084,268
[45] Date of Patent: Jan. 28, 1992

[54] TOOTH WHITENING DENTIFRICE

[75] Inventor: Irwin Thaler, Dix Hills, N.Y.

[73] Assignee: Dental Concepts, Inc., Elmsford, N.Y.

[21] Appl. No.: 716,123

[22] Filed: Jun. 17, 1991

[51] Int. Cl.$^5$ ............... A61K 7/20; A61K 33/40
[52] U.S. Cl. .................... 424/53; 424/62; 424/613; 424/616; 514/900; 514/901; 514/902; 514/944
[58] Field of Search ............ 424/53, 62, 613, 616; 514/900, 944

[56] References Cited

U.S. PATENT DOCUMENTS

| 3,499,844 | 3/1970 | Kibbel et al. | 424/62 |
| 3,892,853 | 7/1975 | Cobble | 424/58 |
| 4,405,599 | 9/1983 | Smigel | 424/53 |
| 4,485,091 | 11/1984 | Fitton | 424/62 |
| 4,528,180 | 7/1985 | Schaeffer | 424/53 |
| 4,537,778 | 8/1985 | Clipper et al. | 424/53 |
| 4,684,517 | 8/1987 | Clipper et al. | 424/53 |
| 4,687,663 | 8/1987 | Schaeffer | 424/53 |
| 4,837,008 | 6/1989 | Rudy et al. | 424/53 |
| 4,839,157 | 6/1989 | Ng | 424/53 |
| 4,983,380 | 1/1991 | Yarborough | 424/52 |
| 5,000,942 | 3/1991 | Libin | 424/53 |

FOREIGN PATENT DOCUMENTS

| 325267 | 7/1989 | European Pat. Off. |
| 90/09165 | 8/1990 | PCT Int'l Appl. |
| 1539771 | 2/1979 | United Kingdom |
| 2068225 | 8/1981 | United Kingdom |
| 2076285 | 12/1981 | United Kingdom |
| 2076286 | 12/1981 | United Kingdom |

OTHER PUBLICATIONS

Kibbel CA.72:125073u (1970) of U.S. Pat. No. 3,499,844 (3/10/70); El-Assasy, GA.85:182368m (1976).
Cobble CA.83:136932b (1975) of U.S. Pat. No. 3,892,853 (7/1/75); Fitton, CA.91:78769f of Gt. Br. 1539771 (2/7/79).
Quinoderm CA.94:52996g (1980) of FR. 2443837 (7/11/80); Fitton, CA.96:91679z (1981) of GT. BR. 2076286 (12/2/81).
Fisher CA.96:91680R (1981) of GT. BR. 2076285 (12/2/81); Quinoderm CA.100:39545g (1983).
Schaeffer CA.103:128825k (1985) of U.S. Pat. No. 4,528,180 (7/9/85); Schaeffer CA.108:173389k (1986) of EP. 202359 (11/26/86).
Rudy et al. CA.111:160024z (1989) of U.S. Pat. No. 4,837,008 (6/6/89); Drucker CA. 112:124958u (1989) of EP. 325267 (7/26/89).
Muryama CA.114:149940m (1990) of PCT/WO 9009165 (8/23/90).

Primary Examiner—Shep K. Rose
Attorney, Agent, or Firm—Natter & Natter

[57] ABSTRACT

An abrasive free hydrogen peroxide tooth whitening dentifrice composition comprises a blend of corn starch, sorbitol, hydrogen peroxide, carbomer 940, flavor, sodium lauryl sulfate, sodium saccharin, potassium sorbate, and sodium benzoate in an aqueous base.

15 Claims, No Drawings

TOOTH WHITENING DENTIFRICE

BACKGROUND OF THE INVENTION

1. Field of the Invention

This invention relates generally to dentifrices and more particularly to toothpaste preparations with peroxide compounds as constituents.

2. Background History

The efficacy of peroxide compounds in oral hygiene has been long recognized. Such compounds have proven effective in the treatment of gingivitis, oral lesions, periodontists, herpetic stomatitis and in combatting plaque. Additionally, peroxide compounds have been utilized for oral cosmetic purposes such as tooth whitening which resulted from the bleaching and cleansing of tooth surfaces.

When peroxide compounds were utilized in combination with most conventionally employed constituent ingredients of dentifrices or other oral hygiene preparations, the tendency of the peroxide compounds to react with such other components presented significant problems and difficulties were encountered with respect to providing products which achieved adequate shelf life.

Examples of prior attempts at providing a stable peroxide compound containing dentifrice were found in the disclosures of U.S. Pat. Nos. 4,839,157 and 4,405,599. Such prior toothpaste preparations included various abrasive agents, such as, dicalcium phosphate, calcium carbonate, magnesium carbonate, silica or polyethylene compounds. The use of abrasive constituents in dentifrices containing peroxide compounds resulted in irritation to both tooth and gum surfaces which were compounded by the interaction of the peroxide composition on the abraded surfaces.

SUMMARY OF THE INVENTION

In compendium, the invention comprises a tooth whitening dentifrice of toothpaste or gel consistency comprising a blend of essentially the following ingredients in percent, by weight: Corn Starch from 2% to 35%, Sorbitol, from 5% to 30%, Hydrogen Peroxide, from 0.2% to 10%, Carbomer 940, from 0.25% to 4%, Flavor, from 0.1% to 2%, Sodium Lauryl Sulfate, from 0.2% to 2%, Sodium Saccharin, from 0% to 0.5%, Potassium Sorbate, from 0.1% to 0.25% and Sodium Benzoate from 0.1% to 0.25%.

The composition is formulated by separately mixing and heating deionized water, the Carbomer 940 constituent, a portion of the Corn Starch constituent and the Sorbitol constituent until smooth and well dispersed to constitute in a first phase component. The Sodium Saccharin constituent and Flavor constituents are separately mixed and to constitute a second phase component.

The first phase component is cooled and mixed with the second phase component as well as the balance of the corn starch constituent which constitutes a third phase component.

The Potassium Sorbate, Sodium Benzoate and Sodium Lauryl Sulfate constituents are mixed with deionized water to form a fourth phase component and added to the mixture of the first, second and third phase components. Thereafter, the mixture is further cooled and the Hydrogen Peroxide constituent, which constitutes a fifth phase component, is added and further mixed.

A further procedure for formulating the composition does not employ heat and the entire Corn Starch constituent is employed as the third phase component which is not added until the first phase and second phase components have been combined.

The resulting preparations provide efficacious tooth cleansing and whitening properties as well as other beneficial properties attributable to the employment of the Hydrogen Peroxide constituent without abrasive action and further exhibits a stable shelf life.

From the foregoing summary, it will be appreciated that it is an aspect of the present invention to provide a tooth whitening dentifrice of the general character described which is not subject to the disadvantages of the background history aforementioned.

To provide a tooth whitening dentifrice of the general character described which produces gentle cleansing and bleaching of tooth surfaces while minimizing irritation of tooth surfaces and gum tissue is another aspect of the present invention.

A consideration of the present invention is to provide a tooth whitening dentifrice of the general character described which is relatively low in cost.

A feature of the present invention is to provide a tooth whitening dentifrice of the general character described which maintains stability of peroxide compound constituents over a practical cosmetic product shelf life.

Yet a further consideration of the present invention is to provide a tooth whitening dentifrice of the general character described which may be economically formulated.

Further considerations of the present invention include providing methods of formulating a tooth whitening dentifrice of the general characters described.

To provide a tooth whitening dentifrice of the general character described which is both efficacious and pleasant tasting is yet a further consideration of the present invention.

To provide a tooth whitening dentifrice of the general character described which may be carried in and dispensed from conventional toothpaste or gel containers such as a tube or pump is yet another aspect of the present invention.

Other aspects, features and considerations in part will be obvious and in part will be pointed out hereinafter.

With these ends in view, the invention finds embodiment in the various combinations of elements, arrangements of parts and series of steps by which the aspects, features and considerations aforementioned and certain other aspects, features and considerations are attained, all with reference to the following description of the preferred embodiments and the scope of which will be more particularly pointed out and indicated in the appended claims.

DESCRIPTION OF PREFERRED EMBODIMENTS

The present invention provides a dentifrice of toothpaste or tooth gel consistency particularly adapted for whitening discolored tooth surfaces by bleaching action and which utilizes Hydrogen Peroxide as its bleaching action constituent. More specifically, the tooth whitening dentifrice of the invention comprises a blend of essentially 2 to 35% Corn Starch which functions as a gelling agent, a thickener, a filler and a binder, 5 to 30% Sorbitol which functions as a humectant and sweetening agent, 0.2 to 10% Hydrogen Peroxide which comprises the active bleaching constituent for tooth whitening, 0.25 to 4% Carbomer 940 which comprises a gum and gelling agent for suspending emulsified constituents, 0.1 to 2% essential oils and the like as Flavor, 0.2 to 2% Sodium Lauryl Sulfate which functions as a foaming and surfactant agent, lowering surface tension between tooth enamel and the dentifrice, 0.1 to 0.25% Potassium Sorbate which functions as a preservative, 0.1 to 0.25% Sodium Benzoate which functions as a preservative and deionized water in a sufficient quantity. Additionally, a water softening chelating agent such as EDTA (approximately 0.1%) may be employed.

Typical examples of whitening dentifrices formulated in accordance with the invention are set forth in the following tables;

TABLE

EXAMPLE 1

| Ingredient | Weight in Pounds | Percent |
|---|---|---|
| PHASE 1 | | |
| Deionized Water | 2341.5 | 33.45 |
| EDTA | 7.0 | 0.10 |
| Carbomer 940 | 210.0 | 3.00 |
| Corn Starch | 1050.0 | 15.00 |
| Sorbitol 70% | 140.0 | 20.00 |
| PHASE 2 | | |
| Sodium Saccharin | 14.00 | .20 |
| Flavor | 42.00 | .60 |
| PHASE 3 | | |
| Corn Starch | 1050.00 | 15.00 |
| PHASE 4 | | |
| Deionized Water | 210.00 | 3.00 |
| Potassium Sorbate | 14.00 | .20 |
| Sodium Benzoate | 7.00 | .10 |
| Sodium Lauryl Sulfate | 56.00 | .80 |
| PHASE 5 | | |
| Hydrogen Peroxide 35% | 598.50 | 8.55 |

In accordance with the method of the present invention, the constituent ingredients set forth in the phase 1 table are heated to 80 degrees C. while mixing well with high shear mixing equipment until phase 1 is smooth and well dispersed. The heated Corn Starch constituent in phase 1 functions as a gelling agent. Constituent ingredients of phase 2 are mixed in a separate vessel.

The phase 1 mixture is cooled to 45 degrees C. and the phase 2 mixture as well as the phase 3 constituent (corn starch) are both added and mixing is continued. The phase 3 Corn Starch constituent functions as a filler.

The phase 4 constituents are separately mixed and then added to the mixture of phases 1, 2 and 3. Thereafter, the mixture is cooled to 30 degrees C. and the Hydrogen Peroxide constituent (phase 5) is added and mixed.

The resulting composition assumes a toothpaste like consistency.

EXAMPLE 2

| Ingredient | Percent |
|---|---|
| PHASE 1 | |
| Deionized Water | 61.65 |
| EDTA | 0.10 |
| Carbomer 940 | 3.00 |
| PHASE 2 | |
| Sorbitol 70% | 20.00 |
| Sodium Saccharin | .20 |
| Flavor | .60 |
| PHASE 3 | |
| Corn Starch | 2.00 |
| PHASE 4 | |
| Deionized Water | 3.00 |

EXAMPLE 2-continued

| Ingredient | Percent |
|---|---|
| Potassium Sorbate | .20 |
| Sodium Benzoate | .10 |
| Sodium Lauryl Sulfate | .60 |
| PHASE 5 | |
| Hydrogen Peroxide 35% | 8.55 |

EXAMPLE 3

| Ingredient | Percent |
|---|---|
| PHASE 1 | |
| Deionized Water | 30.65 |
| EDTA | 0.10 |
| Carbomer 940 | 1.00 |
| PHASE 2 | |
| Sorbitol 70% | 20.00 |
| Sodium Saccharin | .20 |
| Flavor | .60 |
| PHASE 3 | |
| Corn Starch | 35.00 |
| PHASE 4 | |
| Deionized Water | 3.00 |
| Potassium Sorbate | .20 |
| Sodium Benzoate | .10 |
| Sodium Lauryl Sulfate | .60 |
| PHASE 5 | |
| Hydrogen Peroxide 35% | 8.55 |

EXAMPLE 4

| Ingredient | Percent |
|---|---|
| PHASE 1 | |
| Deionized Water | 34.65 |
| EDTA | 0.10 |
| Carbomer 940 | 2.00 |
| PHASE 2 | |
| Sorbitol 70% | 30.00 |
| Sodium Saccharin | .20 |
| Flavor | .60 |
| PHASE 3 | |
| Corn Starch | 20.00 |
| PHASE 4 | |
| Deionized Water | 3.00 |
| Potassium Sorbate | .20 |
| Sodium Benzoate | .10 |
| Sodium Lauryl Sulfate | .60 |
| PHASE 5 | |
| Hydrogen Peroxide 35% | 8.55 |

EXAMPLE 5

| Ingredient | Percent |
|---|---|
| PHASE 1 | |
| Deionized Water | 43.25 |
| EDTA | 0.10 |
| Carbomer 940 | 2.00 |
| PHASE 2 | |
| Sorbitol 70% | 20.00 |
| Sodium Saccharin | .20 |
| Flavor | .60 |
| PHASE 3 | |
| Corn Starch | 20.00 |
| PHASE 4 | |
| Deionized Water | 3.00 |
| Potassium Sorbate | .20 |
| Sodium Benzoate | .10 |
| Sodium Lauryl Sulfate | 2.00 |
| PHASE 5 | |
| Hydrogen Peroxide 35% | 8.55 |

In formulating the tooth whitening dentifrice of examples 2 through 5, the phase 1 constituents are combined and mixed with high shear mixing equipment until the Carbomer 940 is smooth and well dispersed.

In a separate vessel, the phase 2 constituents are separately mixed and the phase 2 mixture is added to the phase 1 mixture. Thereafter, the batch is transferred to a Hobart mixer and the phase 3 constituent (Corn Starch) is added during mixing and mixing is continued until the batch is smooth.

The phase 4 constituents are premixed and added to the batch and mixing of the batch is continued. Thereafter, the phase 5 constituent (Hydrogen Peroxide) is slowly added and mixed until well dispersed.

Shelf life stability of the formulation of each example has been established by determining the percentage of actual Hydrogen Peroxide present utilizing USP XVII Assay Procedure. A three percent (3%) actual Hydrogen Peroxide content has been proven efficacious in tooth whitening. The percentage of actual Hydrogen Peroxide content in the formulations of examples 1 through 5 after initial formulation and after accelerated aging at 43 degrees C. is set forth in the following table:

| EXAMPLE | ACTUAL HYDROGEN PEROXIDE CONTENT | | NUMBER OF DAYS AGED |
|---|---|---|---|
| | INITIAL | AGED AT 43 DEGREES C. | |
| 1 | 3.0% | 2.95% | 9 |
| 2 | 2.95% | 2.90% | 7 |
| 3 | 3.05% | 3.10% | 7 |
| 4 | 3.10% | 2.95% | 7 |
| 5 | 3.05% | 3.00% | 7 |

The tooth whitening dentifrice formulations of the present invention have thus exhibited projected shelf life stability.

The tooth whitening dentifrice formulations in accordance with the present invention are of toothpaste or gel consistency and may be packaged and dispensed from toothpaste tube or pump type containers or dispensers. A sufficient quantity is placed directly upon a toothbrush, preferably a dry toothbrush, and exposed stained tooth surfaces are brushed gently for up to one minute. The mouth is thereafter rinsed. Daily brushing for an initial two week period has proven effective in whitening teeth. Thereafter, a maintenance program of applications once or twice a week is sufficient in preventing further discoloration of tooth surfaces.

Thus, it will be seen that there is provided a tooth whitening dentifrice and a method of formulating such dentifrice which achieves the various aspects, features and considerations of the present invention and which is well suited to meet the conditions of practical usage.

Since various possible embodiments might be made of the invention described herein and various changes might be made of the exemplary embodiments set forth, it is to be understood that all matters described are to be interpreted as illustrative and not in a limiting sense.

Having thus described the invention it is claimed that is new and desired to be secured by letter patent:

1. A stable hydrogen peroxide dentifrice free of abrasive constituents and having a toothpaste consistency, the dentifrice comprising about 0.2 to 10% by weight hydrogen peroxide tooth bleaching agent, about 0.25 to 4% by weight, carbomer 940 gelling agent, about 2 to 35% by weight, corn starch filler, a humectant, a sweetening agent, a surfactant, a preservative and a flavor.

2. A stable hydrogen peroxide dentifrice as constructed in accordance with claim 1 wherein the humectant comprises about 5 to 30% by weight sorbitol.

3. A stable hydrogen peroxide dentifrice as constructed in accordance with claim 1 wherein the sweetening agent comprises about 5 to 30% by weight sorbitol.

4. A stable hydrogen peroxide dentifrice as constructed in accordance with claim 1 wherein the sweetening agent comprises about 0.2% by weight sodium saccharin.

5. A stable hydrogen peroxide dentifrice as constructed in accordance with claim 1 wherein the surfactant comprises about 0.2 to 2% by weight sodium lauryl sulfate.

6. A stable hydrogen peroxide dentifrice as constructed in accordance with claim 1 wherein the preservative comprises about 0.1 to 0.25% potassium sorbate.

7. A stable hydrogen peroxide dentifrice as constructed in accordance with claim 1 wherein the preservative comprises about 0.1 to 0.25% sodium benzoate.

8. A tooth whitening dentifrice composition consisting essentially of, in percent by weight;

| Corn Starch: | 2 to 35% |
|---|---|
| Sorbitol: | 5 to 30% |
| Hydrogen Peroxide: | .2 to 10% |
| Carbomer 940: | .25 to 4% |
| Flavor: | .1 to 2% |
| Sodium Lauryl Sulfate: | .2 to 2% |

9. A tooth whitening dentifrice as constructed in accordance with claim 8 further including 0.2% by weight sodium saccharin.

10. A tooth whitening dentifrice as constructed in accordance with claim 8 further including water in an amount from 35% to 65% by weight.

11. A method of formulating the tooth whitening dentifrice as set forth in claim 10 comprising the steps of:
a) mixing the carbomer 940 in a major portion of the water to form a first phase,
b) separately mixing the sorbitol, the sodium saccharin and the flavor to form a second phase,
c) mixing the first and second phases,
d) adding the corn starch as a third phase and mixing until smooth,
e) separately mixing the sodium lauryl sulfate and a preservative with the remaining portion of the water to form a fourth phase,
f) mixing the fourth phase with the combined first, second and third phases and,
g) adding the hydrogen peroxide as a fifth phase and mixing until well dispersed.

12. A method of formulating the tooth whitening dentifrice as set forth in claim 10 comprising the steps of:
a) mixing and heating the carbomer 940, the sorbitol and approximately one-half of the corn starch with a major portion of the water until smooth and well dispersed to form a first phase,
b) separately mixing the sodium saccharin and the flavor to form a second phase,
c) mixing the first and second phases after cooling the first phase,
d) adding the remaining corn starch as a third phase and mixing, e) separately mixing the sodium lauryl sulfate and a preservative with the remaining portion of the water to form a fourth phase, f) mixing the fourth phase into the mixed first, second and third phases, g) cooling the mixture of the first, second, third and fourth phases, and h) adding the hydrogen peroxide as a fifth phase and mixing until well dispersed.

13. A method of formulating a tooth whitening dentifrice as set forth in claim 12 wherein the first phase is heated to 80 degrees C.

14. A method of formulating a tooth whitening dentifrice as set forth in claim 13 wherein the first phase is cooled to approximately 45 degrees C. prior to adding the second phase and the third phase.

15. A method of formulating a tooth whitening dentifrice as set forth in accordance with claim 14 wherein the mixed first, second, third and fourth phases is cooled to 30 degrees C. prior to adding the hydrogen peroxide.

* * * * *